United States Patent
Igarashi et al.

(10) Patent No.: US 10,016,231 B2
(45) Date of Patent: Jul. 10, 2018

(54) MEDICAL APPARATUS

(71) Applicant: OLYMPUS CORPORATION, Tokyo (JP)

(72) Inventors: Makoto Igarashi, Hachioji (JP); Takeshi Watanabe, Tama (JP); Yuji Hirai, Sagamihara (JP); Kenichi Kimura, Hachioji (JP); Satoshi Homma, Hino (JP); Hiroshi Miyajima, Hachioji (JP); Hiroyoshi Yajima, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/585,515

(22) Filed: May 3, 2017

(65) Prior Publication Data

US 2017/0231689 A1 Aug. 17, 2017

Related U.S. Application Data

(63) Continuation of application No. PCT/JP2016/059153, filed on Mar. 23, 2016.

(30) Foreign Application Priority Data

Apr. 22, 2015 (JP) .................. 2015-087815

(51) Int. Cl.
*A61N 5/06* (2006.01)
*A61B 18/14* (2006.01)
(Continued)

(52) U.S. Cl.
CPC ........ *A61B 18/1445* (2013.01); *A61B 5/0084* (2013.01); *A61B 5/489* (2013.01);
(Continued)

(58) Field of Classification Search
CPC ..... A61B 5/0084; A61B 5/4836; A61B 5/489; A61B 17/00234; A61B 18/1445;
(Continued)

(56) References Cited

U.S. PATENT DOCUMENTS 6,500,113 B2    12/2002  Vilos
2001/0012605 A1  8/2001  Kawamura
(Continued)

FOREIGN PATENT DOCUMENTS

EP    1125543 A2     8/2001
JP    2001-212161 A  8/2001
(Continued)

OTHER PUBLICATIONS

International Search Report dated May 17, 2016 issued in PCT/JP2016/059153.
(Continued)

*Primary Examiner* — Michael Carey
(74) *Attorney, Agent, or Firm* — Scully, Scott, Murphy & Presser, P.C.

(57) ABSTRACT

A medical apparatus includes a treatment device configured to be capable of treating a subject by applying energy to the subject, an optical fiber including a light emitting face for emitting light into the subject, the optical fiber being connected to the treatment device, and a shield portion that is disposed in front of the light emitting face of the optical fiber, the shield portion being configured to expose the light emitting face when the treatment device does not perform a treatment operation and to shield the light emitting face when the treatment device performs the treatment operation.

6 Claims, 14 Drawing Sheets

(51) Int. Cl.
*A61B 5/00* (2006.01)
*A61B 17/00* (2006.01)
*A61B 90/30* (2016.01)
*A61B 90/70* (2016.01)
*A61B 18/00* (2006.01)

(52) U.S. Cl.
CPC ...... *A61B 5/4836* (2013.01); *A61B 17/00234* (2013.01); *A61B 90/30* (2016.02); *A61B 90/70* (2016.02); *A61B 2017/00296* (2013.01); *A61B 2018/0063* (2013.01); *A61B 2018/00601* (2013.01); *A61B 2090/306* (2016.02); *A61B 2218/005* (2013.01); *A61B 2218/008* (2013.01); *A61B 2505/05* (2013.01); *A61B 2562/0238* (2013.01); *A61B 2562/18* (2013.01)

(58) Field of Classification Search
CPC ............... A61B 90/30; A61B 90/70; A61B 2017/00296; A61B 2018/00601; A61B 2018/0063; A61B 2090/306; A61B 2218/005; A61B 2218/008; A61B 2505/05; A61B 2562/0238; A61B 2562/18
USPC .......................................................... 607/62
See application file for complete search history.

(56) References Cited

U.S. PATENT DOCUMENTS

| | | |
|---|---|---|
| 2002/0065450 A1 | 5/2002 | Ogawa |
| 2004/0064015 A1 | 4/2004 | Goto et al. |
| 2005/0033388 A1* | 2/2005 | Brugger ............ A61B 18/20 607/89 |
| 2006/0206118 A1 | 9/2006 | Kim et al. |
| 2006/0265035 A1* | 11/2006 | Yachi ............ A61B 17/320092 607/101 |
| 2007/0219604 A1* | 9/2007 | Yaroslavsky ........ A61N 5/0613 607/100 |
| 2009/0270686 A1 | 10/2009 | Duke et al. |

FOREIGN PATENT DOCUMENTS

| | | |
|---|---|---|
| JP | 2004-057815 A | 2/2004 |
| JP | 2006-341066 A | 12/2006 |
| JP | 2014-097093 A | 5/2014 |
| WO | WO 98/043531 A1 | 10/1998 |
| WO | WO 2006/099285 A2 | 9/2006 |
| WO | WO 2013/134411 A1 | 9/2013 |
| WO | 2014/064607 A1 | 5/2014 |

OTHER PUBLICATIONS

Extended Supplementary European Search Report dated May 16, 2018 in European Patent Application No. 16 78 2918.3.

* cited by examiner

SENSING LASER LIGHT

SENSING LASER LIGHT

AIR FEEDING

MEDICAL APPARATUS

CROSS REFERENCE TO RELATED APPLICATION

This application is a continuation application of PCT/JP2016/059153 filed on Mar. 23, 2016 and claims benefit of Japanese Application No. 2015-087815 filed in Japan on Apr. 22, 2015, the entire contents of which are incorporated herein by this reference.

BACKGROUND OF INVENTION

1. Field of the Invention

The present invention relates to a medical apparatus configured to prevent dirt arising as a result of a dissection operation of a treatment device from blocking light emitted from a light emitting face to a subject.

2. Description of the Related Art

For example, in laparoscopic surgery, avoiding intraoperative bleeding is a basic user need.

Thus, if a blood vessel can be visually recognized, surgery will become more safe and simplified.

Devices having a function of sensing a blood vessel with laser or other light have been previously disclosed.

For example, WO2013/134411 discloses a device having a function of sensing a blood vessel with laser or other light. In particular, WO2013/134411 describes that the device includes a laser Doppler velocimeter, produces an alarm signal when a blood vessel having a diameter greater than a threshold is detected, and produces an alarm display, an LED at a distal end of the device can illuminate, blink and change color, and an energy applicator is stopped based on a sensing value (an off control of an on/off control is performed).

When a treatment device applies energy to a subject to perform dissection or other treatment, a fat tissue irradiated with the energy may evaporate to produce smoke or mist, or body fluid (blood, for example) may be scattered. If the substance arising from the subject (mist, smoke, body fluid (blood, for example) or the like) is deposited on a laser light emitting face, the power of the emitted laser decreases. Return light (reflection light) from the object is also attenuated by the mist or the like, and a sufficient amount of light may be unable to be detected. Thus, if a substance is deposited on the laser light emitting face, a problem arises that the sensitivity of detection of a blood vessel decreases.

As a technique to address such a problem, there is known a technique of removing a substance deposited on a distal end portion of an endoscope by feeding a liquid such as water.

In addition, there has been proposed a technique of removing a substance deposited on a distal end portion of an endoscope by rotating a wiper member disposed on the distal end portion of the endoscope.

Besides, it is common practice to remove an endoscope from inside a body cavity or lumen and wash a distal end portion of the endoscope with hot water or the like or wipes the distal end portion with gauze or the like.

SUMMARY OF THE INVENTION

A medical apparatus according to an aspect of the present invention includes: a treatment device configured to be capable of treating a subject by applying energy to the subject; an irradiation section including a light emitting face for emitting light into the subject, the irradiation section being connected to the treatment device; and a shield portion that is disposed in front of the light emitting face of the irradiation section, the shield portion being configured to expose the light emitting face when the treatment device does not perform a treatment operation and to shield the light emitting face when the treatment device performs the treatment operation.

A medical apparatus according to another aspect of the present invention includes: a treatment device configured to be capable of treating a subject by applying energy to the subject; an irradiation section including a light emitting face for emitting light into the subject, the light emitting face being inserted in the treatment device to protrude from the treatment device; a reciprocating mechanism configured to retract the light emitting face into the treatment device when the treatment device performs a treatment operation and advance the light emitting face to protrude from the treatment device when the treatment device does not perform the treatment operation.

DETAILED DESCRIPTION OF THE PREFERRED EMBODIMENT(S)

In the following, embodiments of the present invention will be described with reference to the drawings.

[First Embodiment]

Figure 1:
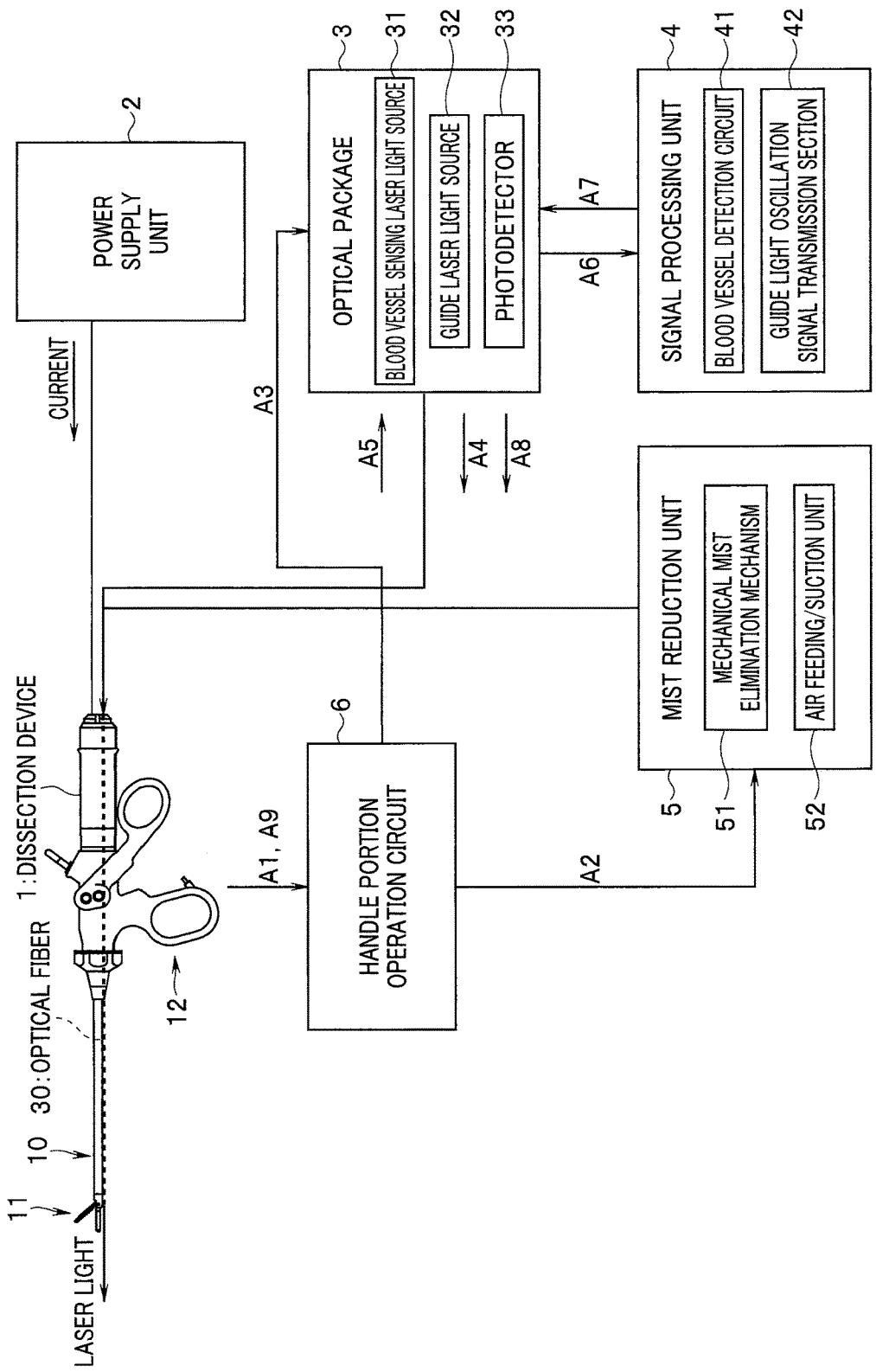
FIG. 1 is a diagram showing an example of a configuration of a medical apparatus according to a first embodiment of the present invention.

FIGS. 1 to 11 show a first embodiment of the present invention. FIG. 1 is a diagram showing an example of a configuration of a medical apparatus.

The medical apparatus according to the present embodiment includes a dissection device 1, a power supply unit 2, an optical package 3, a signal processing unit 4, a mist reduction unit 5, and a handle portion operation circuit 6, for example.

The dissection device 1 is an item to be inserted into a body cavity of a subject, is a treatment device (energy device) configured to be capable of dissecting a tissue of the subject by applying an energy such as heat, light or current to the subject, and may optionally further has a function of performing a sealing treatment on the subject.

The dissection device 1 includes an insertion portion 10 to be inserted into the subject, a treatment portion 11 provided at a distal end portion of the insertion portion 10, and a handle portion 12 for operating the dissection device 1. Furthermore, an optical fiber 30 is arranged to pass through the dissection device 1 from the side of a proximal end of the dissection device 1 toward the distal end portion on the side of the treatment portion 11, for example.

Figure 2:
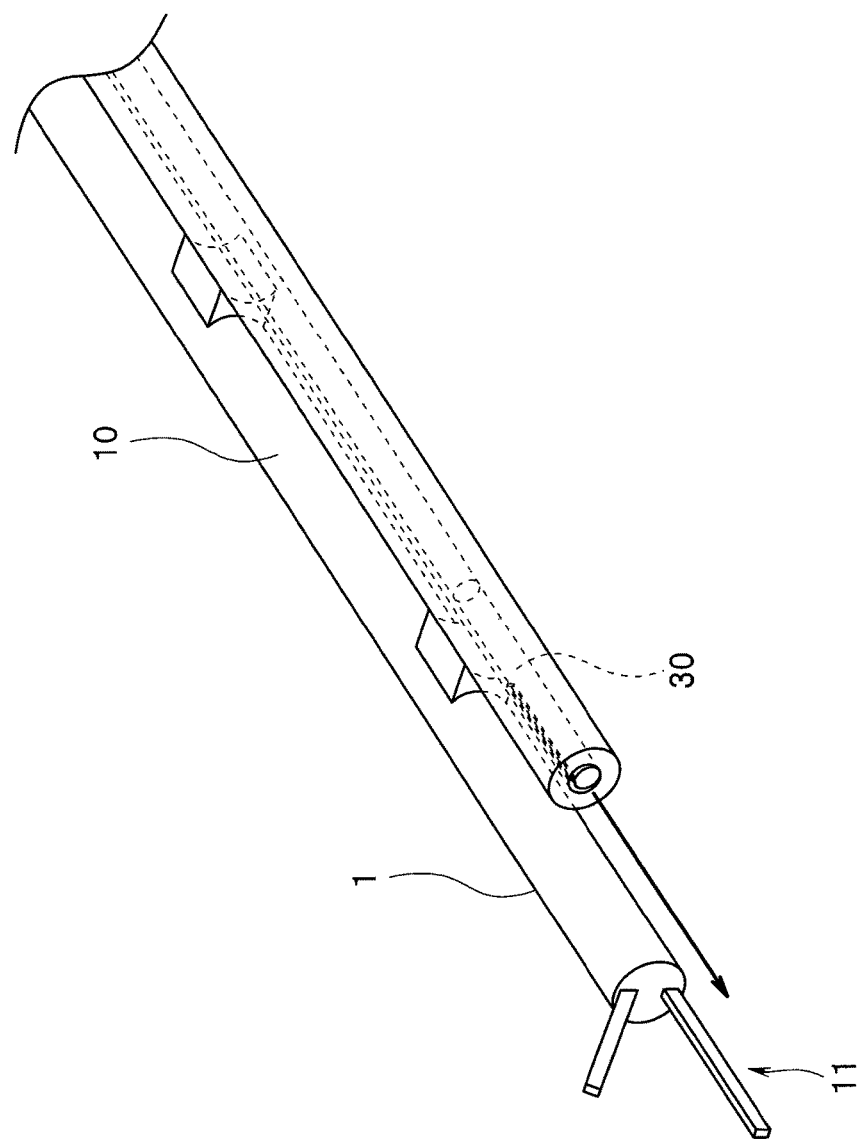
FIG. 2 is a perspective view showing a configuration of a distal end portion of a dissection device according to the first embodiment described above.

FIG. 2 is a perspective view showing a configuration of the distal end portion of the dissection device 1.

At the distal end portion of the insertion portion 10 of the dissection device 1, the treatment portion 11, which includes an upper jaw 11a and a lower jaw 11b that pinch the subject for treatment (see FIG. 4, for example), for example, is disposed. In the vicinity of the treatment portion 11, the optical fiber 30, which is an irradiation section, is disposed in such a manner that a light emitting face 30a (see FIG. 5, for example) at a distal end thereof is exposed (that is, in such a manner that the optical fiber 30 can emit light (laser light, for example) toward the subject).

The power supply unit 2 supplies energy for treatment to the dissection device 1 in the form of an electric current, for example.

The optical package 3, to which the optical fiber 30 described above is connected at the proximal end side thereof, supplies laser light to the optical fiber 30. More specifically, the optical package 3 includes a blood vessel sensing laser light source 31, a guide laser light source 32, and a photodetector 33.

The blood vessel sensing laser light source 31 is configured as a semiconductor light source unit and is a light source section configured to generate laser light to be applied to the subject from the light emitting face 30a and supply the laser light to the optical fiber 30 that is the irradiation section. The laser light generated by the blood vessel sensing laser light source 31 is transmitted through the optical fiber 30 and applied to the subject from the light emitting face 30a, and thus is used as illumination light (sensing laser light) for detecting a blood vessel in the subject.

The guide laser light source 32 is an informing section that informs that a blood vessel is detected by applying light to the detected blood vessel if a blood vessel is detected by a blood vessel detection circuit 41 described later. More specifically, the guide laser light source 32 generates guide laser light (referred to also as guide light as appropriate) serving as informing light as a guide to the detected blood vessel. The guide light is also applied to the subject via the optical fiber 30. An image of the subject irradiated with the guide light is picked up and captured by an endoscope, such as a laparoscope (laparo), that is to be inserted into the body cavity of the subject along with the dissection device 1 and observed on a monitor or the like that displays an endoscopic image and various kinds of information.

The photodetector 33 is a detection section that detects return light (reflection light), from the body cavity of the subject, of the sensing laser light applied by the blood vessel sensing laser light source 31 that is the light source section.

The signal processing unit 4 analyzes the sensing laser light applied by the optical package 3 and the return light from the subject to judge the presence or absence of a blood vessel of the subject, and controls the optical package 3 to apply the guide light if the signal processing unit 4 judges that there is a blood vessel. Specifically, the signal processing unit 4 includes the blood vessel detection circuit 41 and a guide light oscillation signal transmission section 42.

The blood vessel detection circuit 41 is a blood vessel detection section that judges the presence or absence of a blood vessel based on scattering information about blood cells (specifically, red blood cells containing hemoglobin) in a blood vessel (a Doppler frequency spectrum based on a blood flow velocity or the like (referred to simply as a frequency spectrum, hereinafter)) based on a detection signal outputted from the photodetector 33.

The guide light oscillation signal transmission section 42 transmits a trigger signal that causes oscillation of guide light to the guide laser light source 32 in the optical package 3 if the blood vessel detection circuit 41 judges that there is a blood vessel.

The mist reduction unit 5 is to reduce deposition of a substance arising from the subject, such as smoke, mist or body fluid (blood, for example), on the laser light emitting face 30a. The substance, such as smoke, mist or body fluid (blood, for example), arises from the subject (fat tissue, for example) irradiated with energy when the dissection device 1 applies energy to the subject for dissection or other treatments.

Although FIG. 1 shows the mist reduction unit 5 and the dissection device 1 as separate components, the present invention is not limited to this arrangement. The mist reduction unit 5 and the dissection device 1 may be integrated with each other, or a part of the mist reduction unit 5 may be integrated with the dissection device 1, and another part of the mist reduction unit 5 may be separate from the dissection device 1.

The mist reduction unit 5 is a dirt deposition prevention section configured to prevent dirt from being deposited on the light emitting face 30a of the optical fiber 30 in association with a dissection operation of the dissection device 1 (for example, in association with output of energy or in association with opening and closing of the upper jaw 11a and the lower jaw 11b of the treatment portion 11). For example, the mist reduction unit 5 includes at least one of a mechanical mist elimination mechanism 51 and an air feeding/suction unit 52.

The mechanical mist elimination mechanism 51 is a mechanical mechanism that mechanically prevent a substance arising from the subject as a result of the dissection operation of the dissection device 1 (as a representative of the substance, a simple term "mist MST" will be used as appropriate hereinafter (see FIG. 12, for example)) from being deposited on the light emitting face 30a.

The air feeding/suction unit 52 is to reduce deposition of mist MST on the light emitting face 30a by sucking and discharging mist MST with a suction mechanism or to reduce deposition of the mist MST on the light emitting face 30a by feeding air into the subject with air feeding mechanism to reduce a mist concentration in the subject.

Details of a configuration and an operation of the mechanical mist elimination mechanism 51 and the air feeding/suction unit 52 will be described later with regard to specific examples.

The handle portion operation circuit 6 receives an operation signal issued in response to an operation of an operation member of the handle portion 12 and transmits a signal responsive to the operation to the optical package 3 or the mist reduction unit 5.

Figure 3:
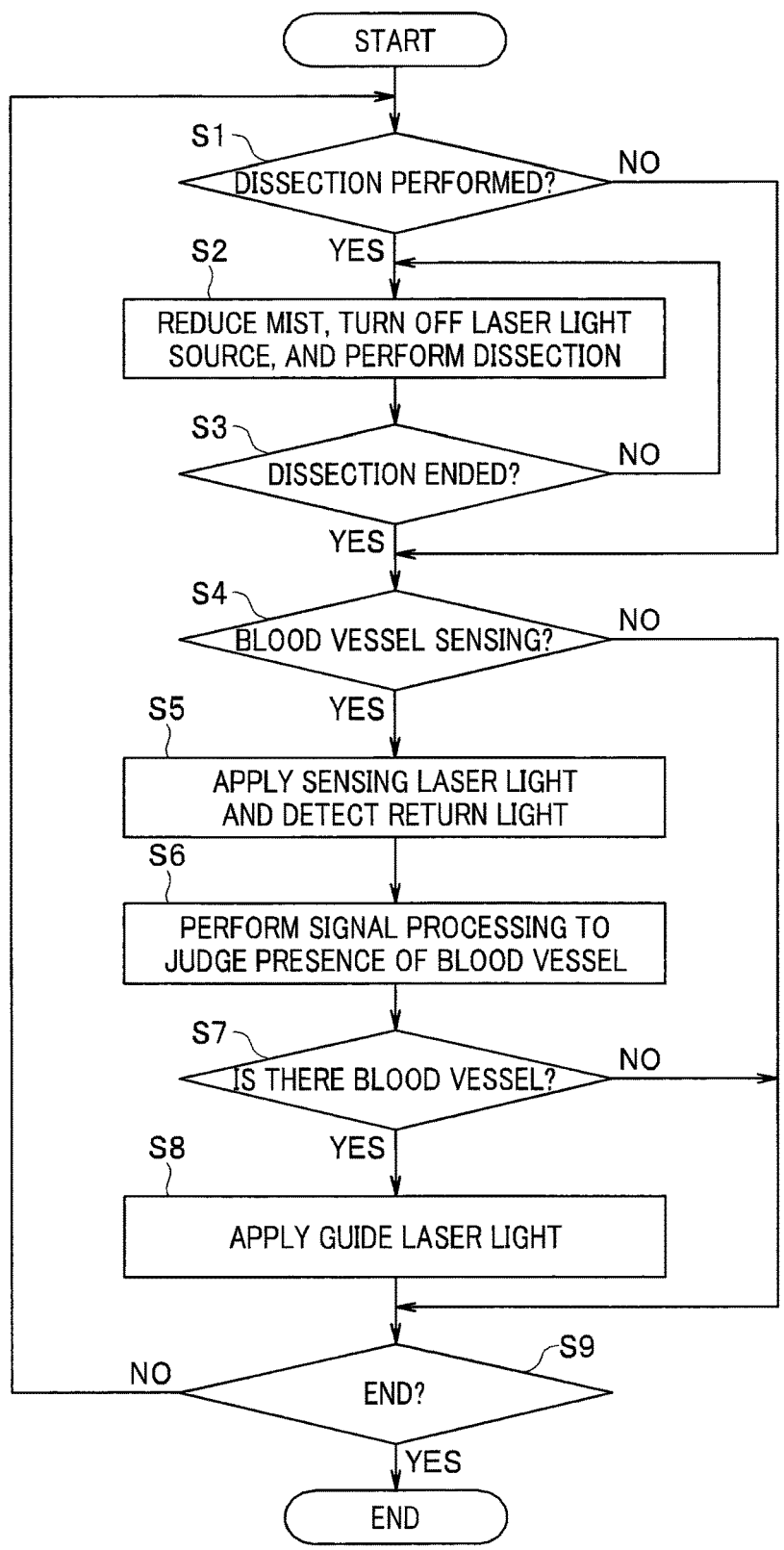
FIG. 3 is a flowchart illustrating an operation of the medical apparatus according to the first embodiment described above.

FIG. 3 is a flowchart illustrating an operation of the medical apparatus.

When the process is started, first, the handle portion operation circuit 6 judges whether or not an operation to cause the dissection device 1 to perform dissection has occurred on the handle portion 12 (Step S1). If the operation member of the handle portion 12 is operated, as shown by the arrows A1 and A9, an operation signal is transmitted to the handle portion operation circuit 6, and the handle portion operation circuit 6 judges the presence or absence of an operation and the kind of the operation based on the received operation signal.

Figure 8:
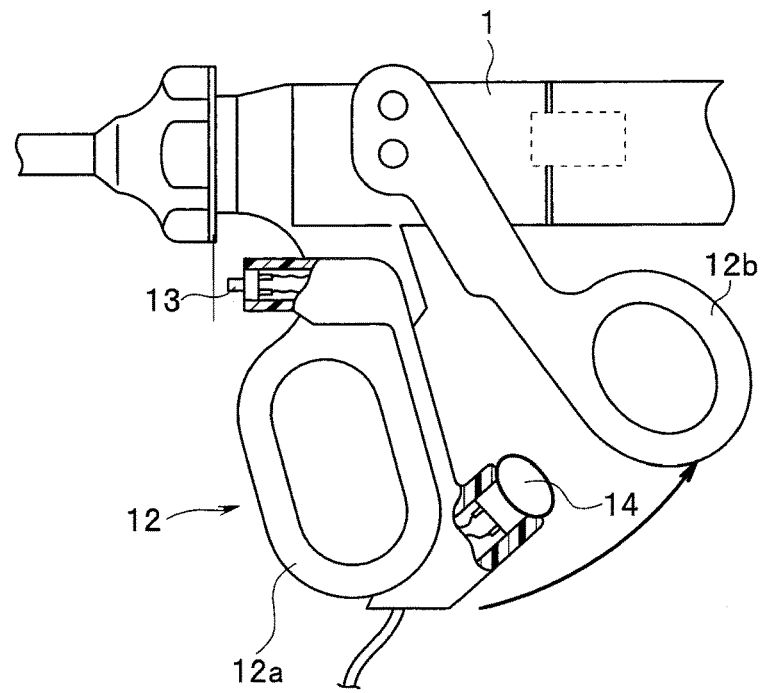
FIG. 8 is a diagram showing an example of an arrangement of operation members around a handle portion of the dissection device involved with dirt deposition prevention in the first embodiment described above.

If it is judged that an operation to perform dissection is performed (by pressing down a second button portion 14 and a third button portion 13 shown in FIG. 8, for example), a dissection operation signal is transmitted from the handle portion 12 to the handle portion operation circuit 6 as shown by the arrow A1, a signal to perform a mist reduction processing is transmitted from the handle portion operation circuit 6 to the mist reduction unit 5 as shown by the arrow A2, and the mist reduction unit 5 performs a mist reduction processing. At the same time, the blood vessel sensing laser light source 31 and the guide laser light source 32 in the optical package 3 are locked in a power off state (only supply of the laser light to the optical fiber 30 may be stopped since, if a power supply is turned off, it takes long to stabilize the laser light when the power supply is turned on again afterwards). The power supply unit 2 then supplies a current to the dissection device 1, and the dissection device 1 performs a dissection operation (Step S2).

After that, it is judged whether or not an operation to cause the dissection device 1 to stop dissection has occurred on the handle portion 12 (Step S3).

If it is judged that no operation to stop dissection has occurred, the process returns to Step S2, and the process described above is performed.

Figure 9:
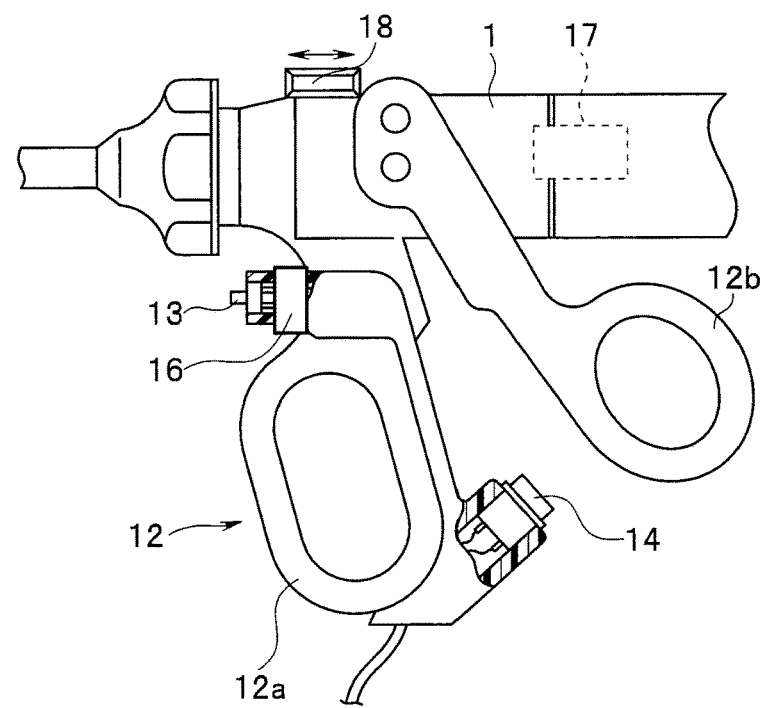
FIG. 9 is a diagram showing another example of the arrangement of operation members around the handle portion of the dissection device involved with the dirt deposition prevention in the first embodiment described above.
Figure 10:
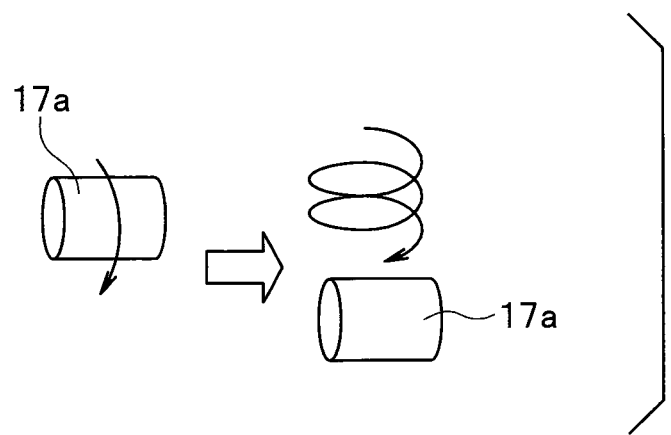
FIG. 10 is an enlarged view for illustrating an example of an operation of an operation member involved with the dirt deposition prevention in the first embodiment described above.
Figure 11:
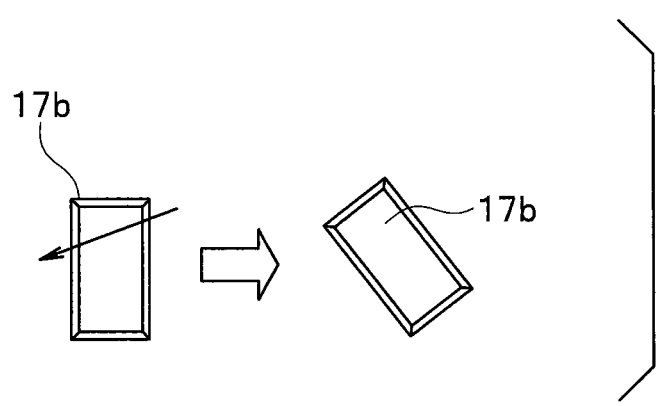
FIG. 11 is an enlarged view for illustrating another example of the operation of the operation member involved with the dirt deposition prevention in the first embodiment described above.

If it is judged in Step S2 that an operation to stop dissection has occurred, or if it is judged in Step S1 that no operation to perform dissection has occurred, it is judged whether or not an operation to perform blood vessel sensing that involves detecting a blood vessel and informing of the presence of the blood vessel (for example, an operation of keeping pressing a dial portion 17a, a first push portion 17b, a second push portion 18, or a first button portion 16 shown in FIGS. 9 to 11 or an operation of a foot switch) has occurred on the handle portion 12 (Step S4). If an operation to perform blood vessel sensing has occurred, an operation signal is transmitted from the handle portion 12 to the handle portion operation circuit 6 as shown by the arrow A9.

If it is judged that an operation to perform blood vessel sensing has occurred, a signal is transmitted from the handle portion operation circuit 6 to the optical package 3 as shown by the arrow A3 to turn on a power supply of the blood vessel sensing laser light source 31 and the guide laser light source 32 in the optical package 3. The blood vessel sensing laser light source 31 emits sensing laser light, which is transmitted through the optical fiber 30 as shown by the arrow A4 and applied to the subject from the light emitting face 30a. Furthermore, the return light from the body cavity of the subject is transmitted through the optical fiber 30 as shown by the arrow A5 and detected by the photodetector 33 (Step S5).

A detection signal of the photodetector 33 is transmitted to the signal processing unit 4 as shown by the arrow A6, and the blood vessel detection circuit 41 judges the presence or absence of a blood vessel (Step S6).

Based on whether the blood vessel detection circuit 41 has judged that there is a blood vessel or not, the process branches (Step S7).

Specifically, if the judgement result is that there is a blood vessel, the guide light oscillation signal transmission section 42 transmits a trigger signal that causes oscillation of guide light to the guide laser light source 32 as shown by the arrow A7 (the trigger signal is not transmitted if it is judged that there is no blood vessel), and the guide laser light source 32 emits guide light. The emitted guide light is transmitted through the optical fiber 30 as shown by the arrow A8 and applied to the subject from the light emitting face 30a (Step S8).

If the judgement result in Step S7 is that there is no blood vessel, or if it is judged in Step S4 that no operation to perform blood vessel sensing has occurred, it is judged whether or not an operation to end this process has occurred (Step S9). If no operation to end the process has occurred, the process returns to Step S1, and the process described above is repeated. If an operation to end the process has occurred, this process is ended.

Next, a configuration of the mist reduction unit 5 according to the present embodiment will be described with reference to FIGS. 4 to 7.

Figure 4:
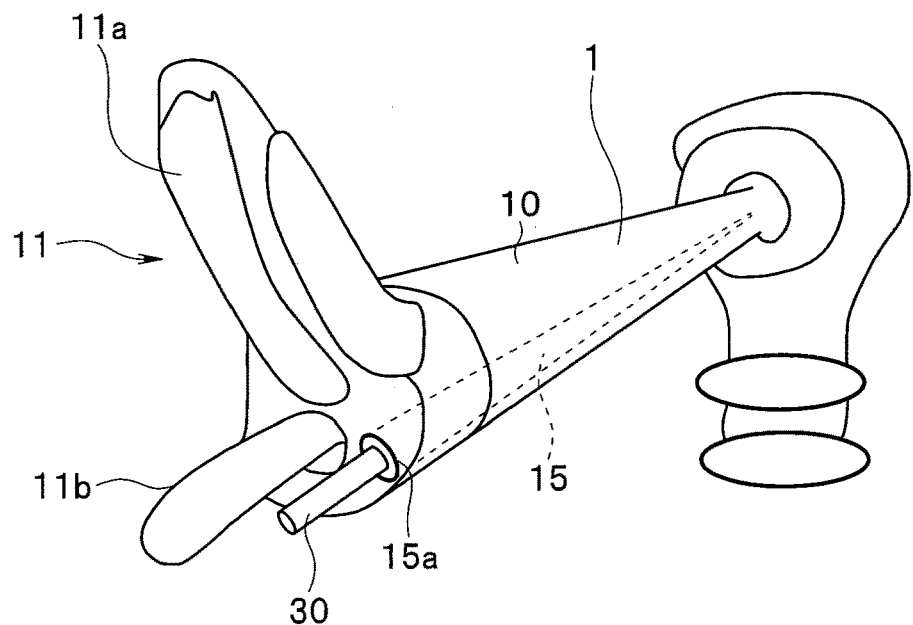
FIG. 4 is a view showing how an optical fiber protrudes from the distal end portion of the dissection device when a dissection operation is not performed in the first embodiment described above.
Figure 5:
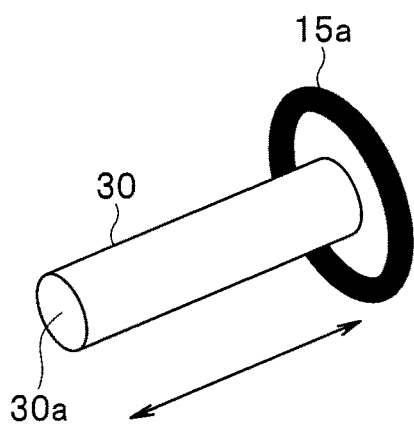
FIG. 5 is an enlarged view showing how the optical fiber protrudes from the distal end portion of the dissection device when the dissection operation is not performed in the first embodiment described above.
Figure 6:
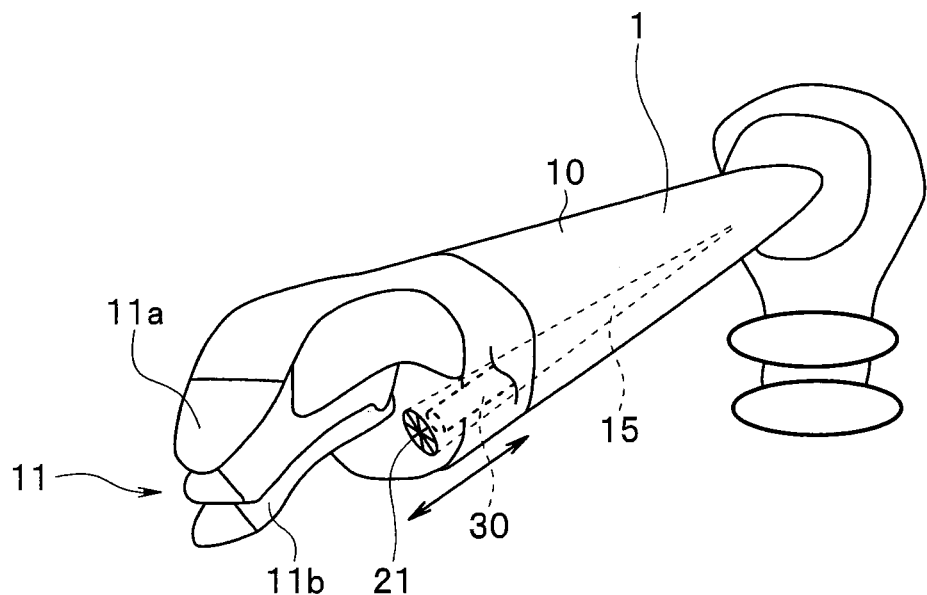
FIG. 6 is a view showing a dirt deposition prevention section when the dissection device is performing the dissection operation in the first embodiment described above.
Figure 7:
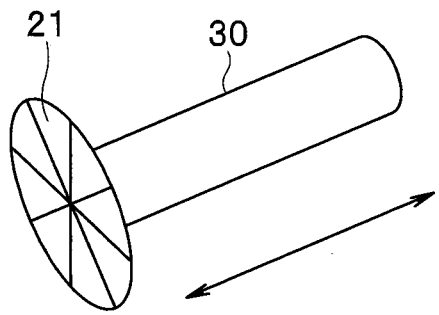
FIG. 7 is an enlarged view showing the dirt deposition prevention section when the dissection device is performing the dissection operation in the first embodiment described above.

FIG. 4 is a view showing how the optical fiber protrudes from the distal end portion of the dissection device 1 when the dissection operation is not performed, FIG. 5 is an enlarged view showing how the optical fiber protrudes from the distal end portion of the dissection device 1 when the dissection operation is not performed, FIG. 6 is a view showing the dirt deposition prevention section when the dissection device 1 is performing the dissection operation, and FIG. 7 is an enlarged view showing the dirt deposition prevention section when the dissection device 1 is performing the dissection operation.

An optical fiber insertion channel 15 is formed in the dissection device 1 so as to extend from the hand side to the distal end side, and the optical fiber 30 is inserted in the optical fiber insertion channel 15. When the dissection device 1 is not performing the dissection operation, as shown in FIGS. 4 and 5, the light emitting face 30a at the distal end of the optical fiber 30 protrudes from a distal end opening 15a of the optical fiber insertion channel 15 and is exposed.

On the other hand, when the dissection device 1 is performing the dissection operation, as shown in FIGS. 6 and 7, the light emitting face 30a at the distal end of the optical fiber 30 is housed in the distal end opening 15a of the optical fiber insertion channel 15.

Thus, according to the present embodiment, the mechanical mist elimination mechanism 51 serving as the dirt deposition prevention section includes a reciprocating mechanism configured to retract the light emitting face 30a into the dissection device 1 when the dissection device 1 performs the dissection operation and advance the light emitting face 30a to protrude from the dissection device 1 when the dissection device 1 does not perform the dissection operation. The reciprocating mechanism is not limited to a particular configuration. The reciprocating mechanism may be configured to operate in association with opening and closing of the upper jaw 11a and the lower jaw 11b that open and close in response to opening and closing of a first handle 12a and a second handle 12b (see FIG. 8, for example) of the handle portion 12, or may be configured to use an appropriate separate drive source, such as a motor or a solenoid plunger.

The mechanical mist elimination mechanism 51 serving as the dirt deposition prevention section according to the present embodiment further includes a wiping portion 21 provided at the distal end opening 15a (however, the mechanical mist elimination mechanism 51 may not include the wiping portion 21 and may be configured to include only the reciprocating mechanism described above). The wiping portion 21 is configured for example as a rubber valve having a plurality of slits extending from the center to the circumference thereof that allow opening and closing of the rubber valve, and a member of gauze or the like that wipes out dirt is affixed to an inner face of the rubber valve facing the optical fiber insertion channel 15.

Thus, the wiping portion 21 is configured to generally block the distal end opening 15a to prevent mist MST from being deposited on the light emitting face 30a when the light emitting face 30a is housed in the distal end opening 15a, and to wipe out mist MST deposited on the distal end opening 15a with the gauze or the like on the inner face thereof when the light emitting face 30a protrudes again from the distal end opening 15a. That is, cleaning of the light emitting face 30a by the gauze or the like on the inner face of the wiping portion 21 occurs each time when the light emitting face 30a protrudes from the distal end opening 15a.

Furthermore, in association with the light emitting face 30a of the optical fiber 30 being housed in the optical fiber insertion channel 15 (that is, in association with the dissection operation by the dissection device 1 being performed), the blood vessel sensing laser light source 31 and the guide laser light source 32 are automatically turned off (Alternatively, only supply of the laser light may be stopped as described above. The same holds true for the following description.) (See Step S2 in FIG. 3). On the other hand, when the light emitting face 30a of the optical fiber 30 protrudes from the distal end opening 15a of the optical fiber insertion channel 15, the sensing laser light is emitted.

In short, at least one of the signal processing unit 4 serving as a control section and the optical package 3 controls the light source section to stop supply of the laser light to the optical fiber 30.

FIG. 8 is a diagram showing an arrangement of operation members around the handle portion 12 of the dissection device 1 involved with the dirt deposition prevention.

The handle portion 12 is an operation portion that performs an operation of dissecting a tissue of the subject and is operated by opening and closing the first handle 12a and the second handle 12b each having a finger ring that are coupled to each other by a hinge mechanism.

As shown in FIG. 8, the third button portion 13 is provided on a proximal end portion (upper end portion) of the first handle 12a on a side facing in a direction of insertion, and the second button portion 14 is provided on a distal end portion (lower end portion) on a side closer to the second handle 12b. The third button portion 13 and the second button portion 14 are provided at positions where the buttons can be (directly or indirectly) operated by a hand holding the handle portion 12.

Specifically, the third button portion 13 is pressed by a finger (an index finger, for example) of a hand of an operator holding the handle portion 12. The second button portion 14 is pressed by a face of the second handle 12b by the operator holding the handle portion 12 with a hand and squeezing the first handle 12a and the second handle 12b (thus, the second button portion 14 is not directly pressed by a finger or hand of the operator but indirectly operated by the operator operating the first handle 12a and the second handle 12b).

Regardless of which is pressed, if one of the third button portion 13 and the second button portion 14 is pressed, the power supply unit 2 supplies energy to the dissection device 1 to perform sealing and cutting or sealing on a tissue of the subject.

The dissection device 1 provided with the operation members shown in FIG. 8 is configured so that the light emitting face 30a of the optical fiber 30 moves into the optical fiber insertion channel 15 in association with any of the operations (a) and (b) described below.

(a) The operator holds the handle portion 12, and the second button portion 14 is pressed by a face of the second handle 12b (see FIG. 8).

(b) The operator presses the third button portion 13 (see FIG. 8).

FIG. 9 is a diagram showing another example of the arrangement of operation members around the handle portion 12 of the dissection device 1 involved with the dirt deposition prevention, FIG. 10 is an enlarged view for illustrating an example of an operation of an operation member involved with the dirt deposition prevention, and FIG. 11 is an enlarged view for illustrating another example of the operation of the operation member involved with the dirt deposition prevention.

In addition to the operation members shown in FIG. 8, as shown in FIG. 9, the first button portion 16 can be provided on a side face of the third button portion 13 of the first handle 12a, a first operation portion 17 can be provided on a side face of a main body supporting the first handle 12a and the second handle 12b at a hand side of the second handle 12b, and a second push portion 18 can be provided on an upper face of the main body supporting the first handle 12a and the second handle 12b.

The first operation portion 17 is configured as a dial portion 17a that can be rotated for operation as shown in FIG. 10, or a first push portion 17b that can be pressed for operation as shown in FIG. 11, for example. The second push portion 18 is configured as a push portion that can be pressed for operation, for example.

The first button portion 16, the first operation portion 17 and the second push portion 18 are also provided at positions where the portions can be operated by the hand holding the handle portion 12. All of the first button portion 16, the first operation portion 17 and the second push portion 18 do not necessarily have to be provided, and it is essential only that one or more of the portions are provided, for example.

If any of the first button portion 16, the first operation portion 17 and the second push portion 18 is operated, the sensing laser light and the guide light are emitted from the optical package 3. However, as described above, emission of the sensing laser light and the guide light is permitted only when the light emitting face 30a of the optical fiber 30 is protruded from the distal end opening 15a of the optical fiber insertion channel 15, and emission of any of the sensing laser light and the guide light is inhibited when the light emitting face 30a is housed in the optical fiber insertion channel 15.

With the dissection device 1 provided with the operation members shown in FIG. 9, the light emitting face 30a of the optical fiber 30 can be moved into the optical fiber insertion channel 15 and mist reduction can be performed in association with not only the operation (a) or (b) described above but also the operation (c) described below.

(c) Any of the first button portion 16, the first operation portion 17, and the second push portion 18 is switched from an operational state to apply the sensing laser light and the guide light to an operational state not to apply the sensing laser light and the guide light. In association with the operation (c), both laser application and mist reduction can be activated by operating only one operation member, and the operation is simplified.

According to the first embodiment, the mist reduction unit 5 that is the dirt deposition prevention section prevents dirt from being deposited on the light emitting face 30a of the optical fiber 30 in association with the dissection operation of the dissection device 1, so that a decrease in intensity of light emitted from the light emitting face 30a to the subject can be suppressed.

Since the dirt deposition prevention occurs in association with the dissection operation, deposition of a substance arising from the subject as a result of the dissection operation of the dissection device 1 can be effectively prevented.

In addition, since the mechanical mist elimination mechanism 51 that is the dirt deposition prevention section is configured to include a reciprocating mechanism configured to retract the light emitting face 30a into the dissection device 1 when the dissection device 1 performs the dissection operation and advance the light emitting face 30a to protrude from the dissection device 1 when the dissection device 1 does not perform the dissection operation, dirt deposition can be effectively reduced.

In addition, since the wiping portion 21 is provided, mist MST can be prevented from being deposited on the light emitting face 30a when the optical fiber 30 is housed in the optical fiber insertion channel 15, and mist MST deposited on the distal end opening 15a can be wiped out when the light emitting face 30a is protruded from the distal end opening 15a.

Since supply of the laser light from the optical package 3 to the optical fiber 30 is stopped when the dissection device 1 performs the dissection operation, that is, when the light emitting face 30a is housed in the optical fiber insertion channel 15, application of unnecessary laser light can be avoided, and occurrence of return light of laser light reflected in the dissection device 1 can also be avoided.

In this way, the medical apparatus capable of applying energy to a subject for treatment and emitting laser or other light for blood vessel recognition is configured to prevent mist MST from being deposited on the light emitting face 30a and thus can maintain high sensitivity of detection of a blood vessel, such as a deep blood vessel.

[Second Embodiment]

Figure 12:
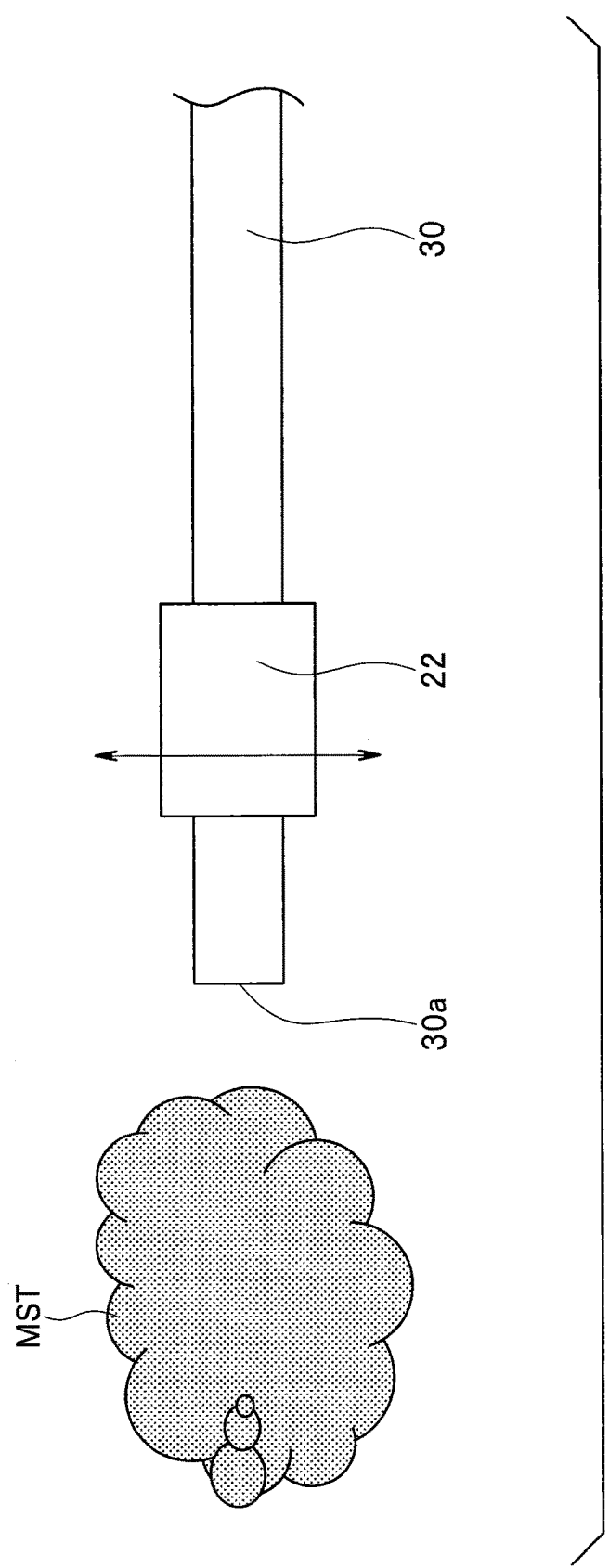
FIG. 12 is a diagram showing a configuration of the dirt deposition prevention section according to a second embodiment of the present invention.
Figure 13:
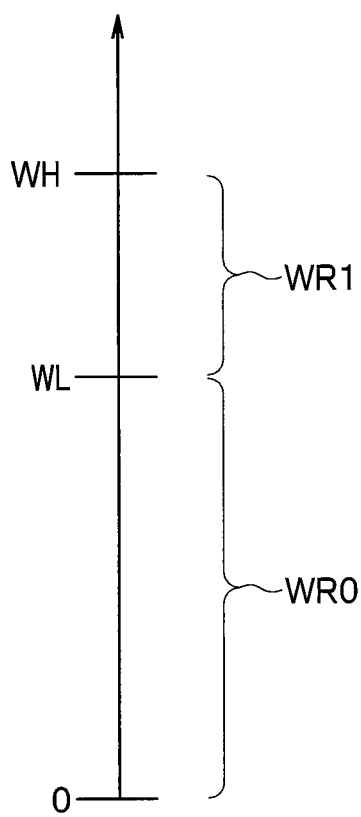
FIG. 13 is a chart showing an example of how an output of a blood vessel sensing laser light source is controlled according to whether the dissection operation of the dissection device occurs or not in the second embodiment described above.

FIGS. 12 and 13 show a second embodiment of the present invention, and FIG. 12 is a diagram showing a configuration of a dirt deposition prevention section.

In the description of the second embodiment, the same parts as those in the first embodiment described above will be denoted by the same reference numerals, and descriptions thereof will be omitted as appropriate, and differences from the first embodiment will be mainly described.

The mechanical mist elimination mechanism 51 according to the present embodiment includes a vibrator portion 22 constituted by an ultrasound vibrator portion (actuator) or the like, which is provided on the distal end of the optical fiber 30. The vibrator portion 22 is fixed by adhesive to an outer surface of the distal end portion of the optical fiber 30 as shown in FIG. 12.

In association with any of the operations (a), (b) and (c) in the first embodiment described above, the vibrator portion 22 is driven to vibrate as shown by the arrow in FIG. 12.

Then, the distal end portion of the optical fiber 30 fixed to the vibrator portion 22 also vibrates, and any dirt due to mist MST on the light emitting face 30a is shaken off and eliminated.

FIG. 13 is a chart showing an example of how the output of the blood vessel sensing laser light source 31 is controlled according to whether the dissection operation of the dissection device 1 occurs or not. The guide laser light source 32 can be controlled in substantially the same manner as the blood vessel sensing laser light source 31, and thus, only the control of the output of the blood vessel sensing laser light source 31 will be described here.

When the vibrator portion 22 is not driven, and a normal blood vessel sensing is performed, a light intensity W of the blood vessel sensing laser light source 31 is set to fall within an intensity range of the sensing laser light for blood vessel sensing, that is, an intensity range WR1 equal to or higher than a minimum intensity WL and equal to or lower than a maximum intensity WH ($WL \leq W \leq WH$).

On the other hand, when the vibrator portion 22 is driven, the light intensity of the sensing laser light of the blood vessel sensing laser light source 31 is set to fall within an intensity range WR0 where the light intensity W satisfies a relation of $0 \leq W < WL$. The intensity range WR0 includes 0, and this means that the blood vessel sensing laser light source 31 can be turned off when the vibrator portion 22 is driven.

Thus, at least one of the signal processing unit 4 serving as the control section and the optical package 3 controls the laser light supplied to the optical fiber 30 to be an output value within a service (sensing) output range (which corresponds to the intensity range WR1) when the dissection device 1 does not perform the dissection operation, and controls the laser light supplied to the optical fiber 30 to be an output value (which corresponds to the intensity range WR0) lower than the service output range when the dissection device 1 performs the dissection operation.

According to the second embodiment, substantially the same effects as in the first embodiment described above can be achieved, and dirt can be removed by an electrical control associated with input of an operation signal from an operation member, since the mechanical mist elimination mechanism 51 that is the dirt deposition prevention section includes the vibrator portion 22 configured to make the light emitting face 30a of the optical fiber 30 vibrate.

In addition, since the output value of the laser light supplied to the optical fiber 30 is lower than the service output range when the vibrator portion 22 is vibrating, power consumption of the blood vessel sensing laser light source 31 and the guide laser light source 32 can be effectively reduced. Furthermore, if the output value is not set at 0 when the vibrator portion 22 is vibrating, the waiting time for the output value of the laser light to return to within the service output range can be reduced.

[Third Embodiment]

Figure 14:
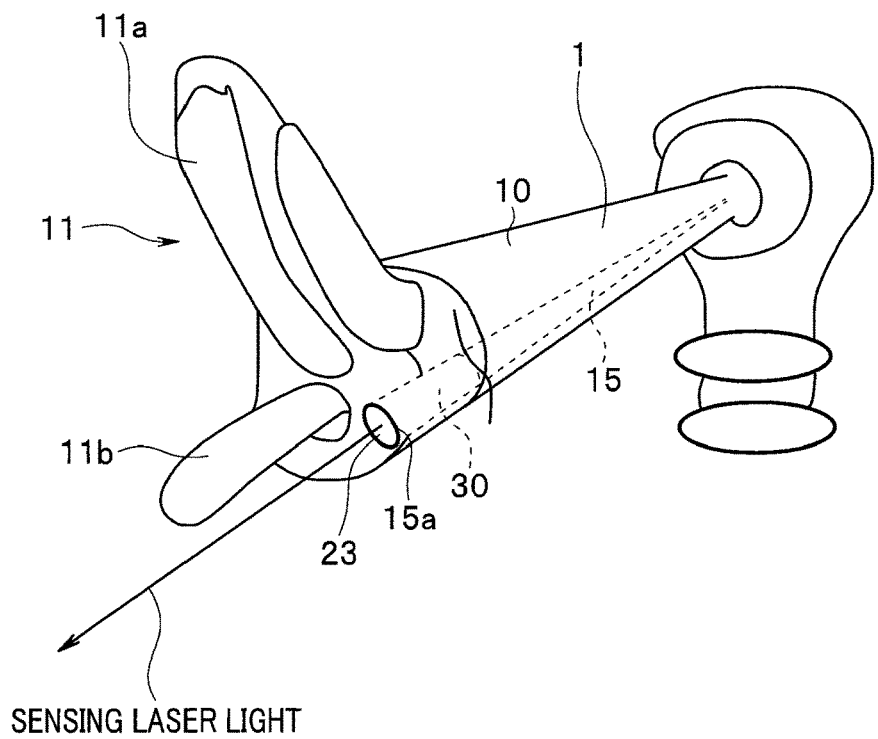
FIG. 14 is a diagram showing the dirt deposition prevention section when the dissection device is not performing the dissection operation in a third embodiment of the present invention.

FIGS. 14 to 18 show a third embodiment of the present invention, and FIG. 14 is a diagram showing the dirt deposition prevention section when the dissection device 1 is not performing the dissection operation.

In the description of the third embodiment, the same parts as those in the first and second embodiments described above will be denoted by the same reference numerals, and descriptions thereof will be omitted as appropriate, and differences from the first and second embodiments will be mainly described.

The mechanical mist elimination mechanism 51 according to the present embodiment includes a shield portion 23 provided at the distal end opening 15a of the optical fiber insertion channel 15. The shield portion 23 is a mechanical mechanism capable of switchably opening and closing the distal end opening 15a and is configured as a shutter mechanism that can be opened and closed, for example.

Figure 15:
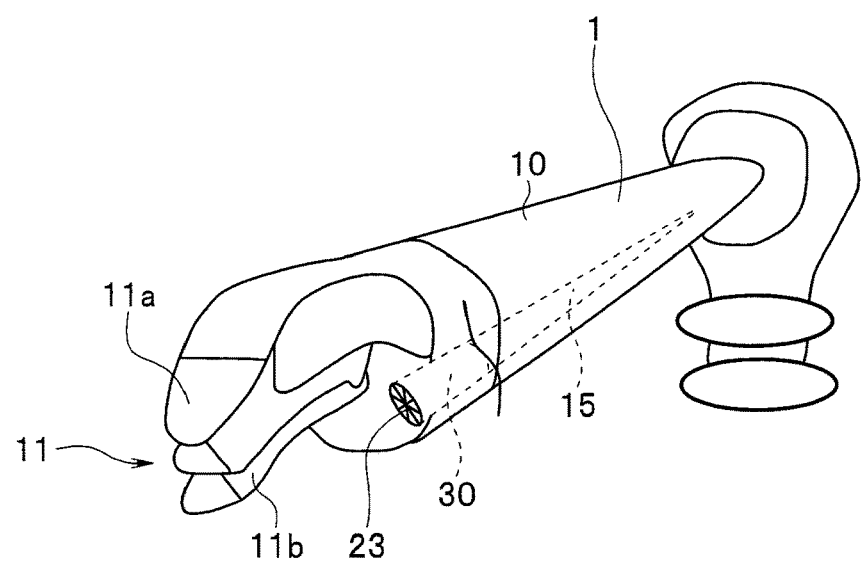
FIG. 15 is a diagram showing the dirt deposition prevention section when the dissection device is performing the dissection operation in the third embodiment described above.

Specifically, when the dissection device 1 is not performing the dissection operation, the shield portion 23 is open as shown in FIG. 14. On the other hand, when the dissection device 1 is performing the dissection operation, the shield portion 23 is closed as shown in FIG. 15.

The shield portion 23 is closed in association with any of the operations (a), (b) and (c) in the first embodiment described above.

As in the first embodiment described above, the blood vessel sensing laser light source 31 and the guide laser light source 32 are automatically turned off in association with the shield portion 23 being closed (see Step S2 in FIG. 3), and the laser light is emitted from the optical package 3 in association with the shield portion 23 being opened.

Figure 16:
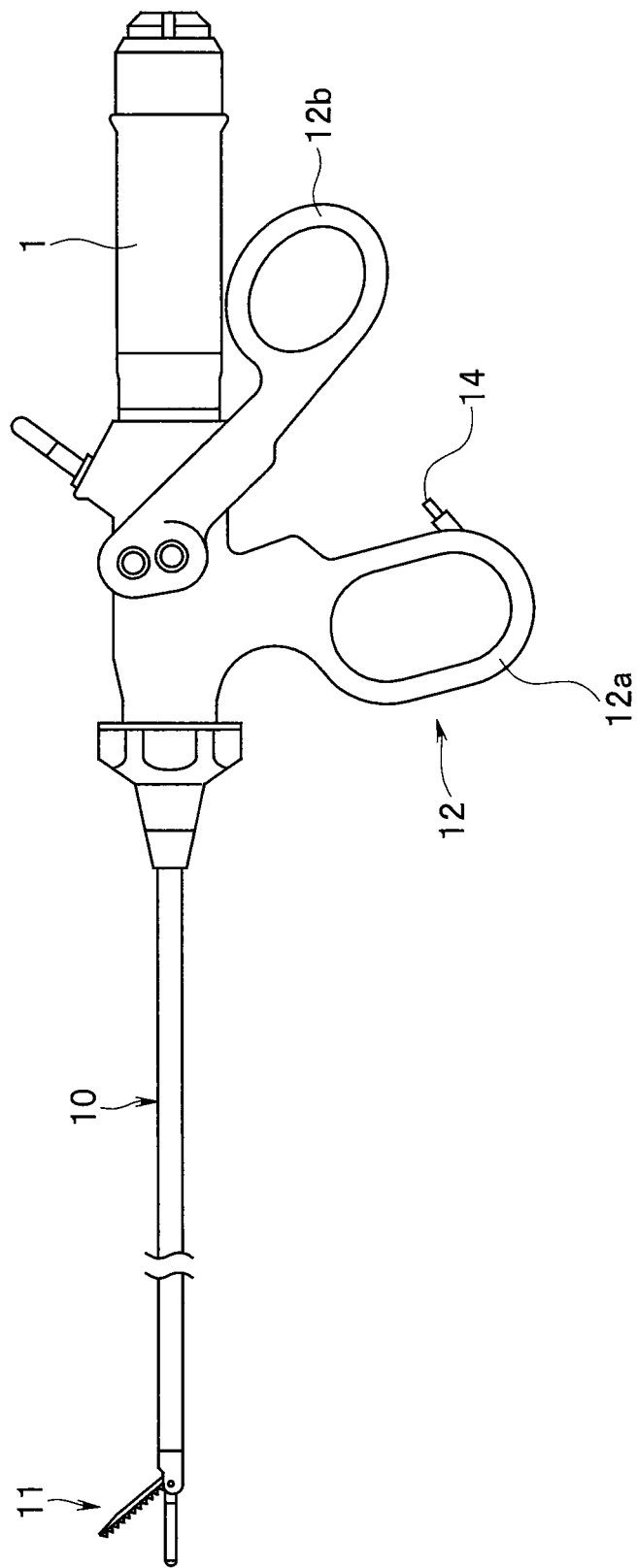
FIG. 16 is a side view showing a configuration of the dissection device according to a modification of the third embodiment described above.
Figure 17:
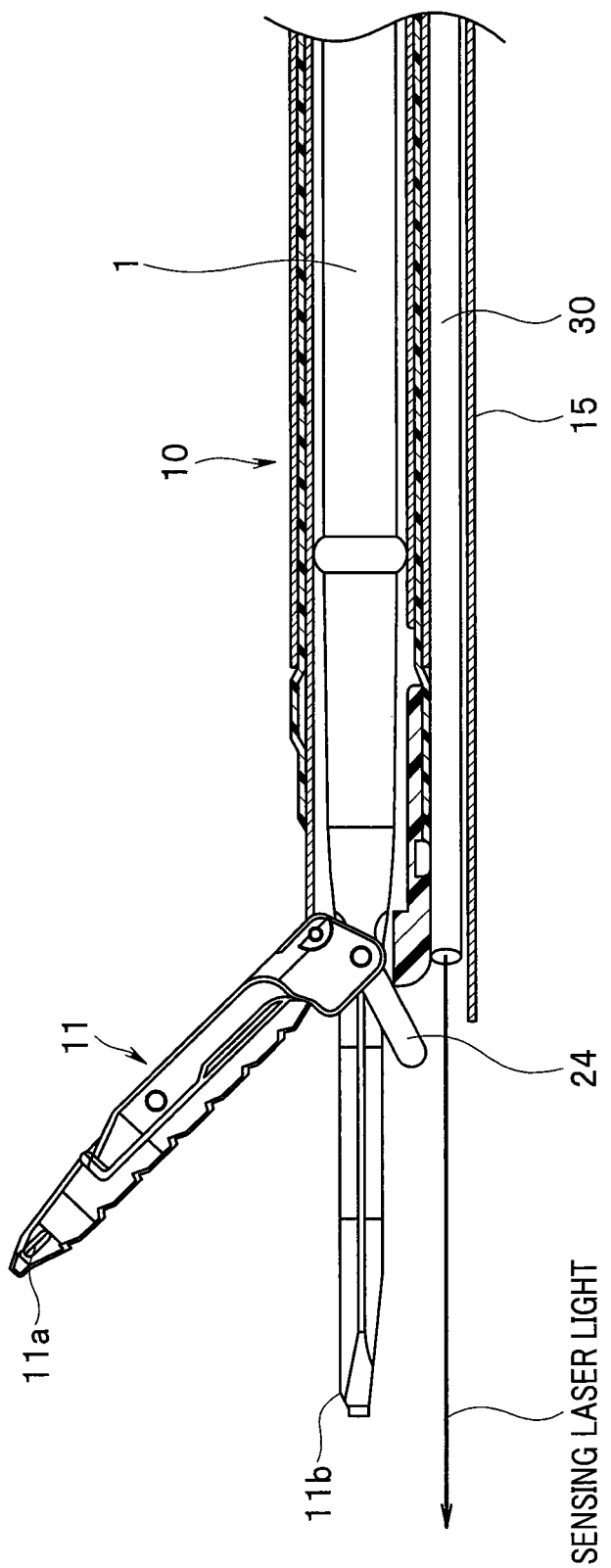
FIG. 17 is a cross-sectional view showing a configuration of the distal end portion of the dissection device when the dissection device is not performing the dissection operation in the modification of the third embodiment described above.
Figure 18:
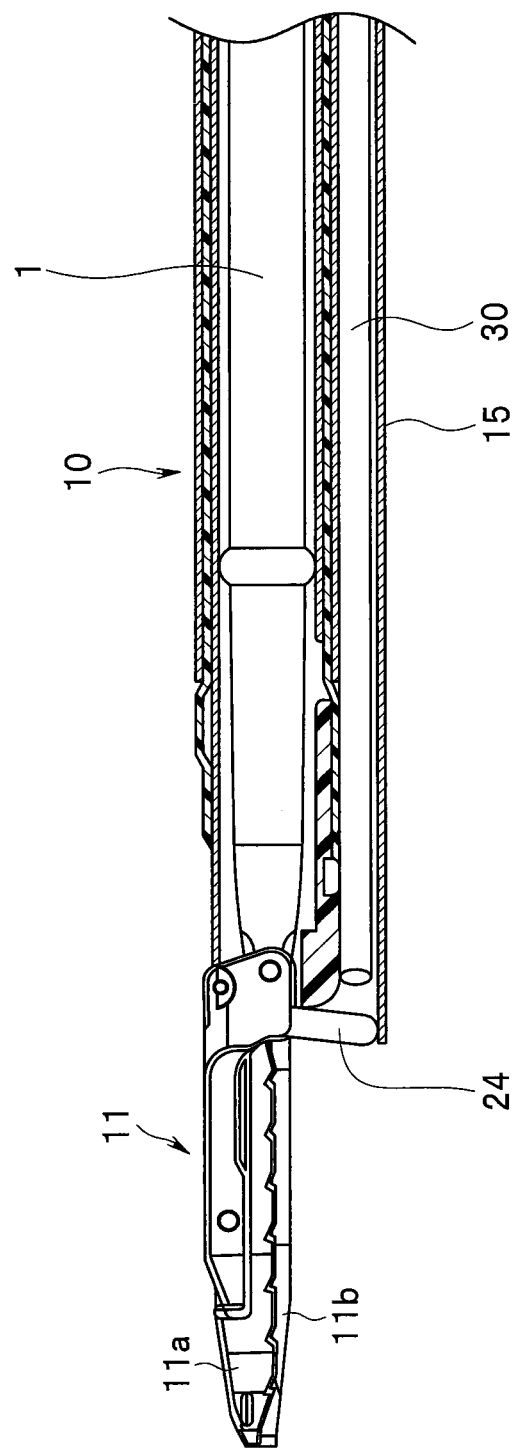
FIG. 18 is a cross-sectional view showing a configuration of the distal end portion of the dissection device when the dissection device is performing the dissection operation in the modification of the third embodiment described above.

Next, modifications of the shield portion will be described with reference to FIGS. 16 to 18. FIG. 16 is a side view showing a configuration of the dissection device 1, FIG. 17 is a cross-sectional view showing a configuration of the distal end portion of the dissection device 1 when the dissection device 1 is not performing the dissection operation, and FIG. 18 is a cross-sectional view showing a configuration of the distal end portion of the dissection device 1 when the dissection device 1 is performing the dissection operation.

The treatment portion 11 provided on the distal end portion of the dissection device 1 shown in FIG. 16 includes the upper jaw 11a and the lower jaw 11b that can be opened and closed described above as shown in FIGS. 17 and 18. Specifically, for example, the lower jaw 11b is formed as an integral (fixed) extension of the insertion portion 10 of the dissection device 1, whereas the upper jaw 11a can be rotated via a hinge mechanism and opened and closed with respect to the lower jaw 11b.

The upper jaw 11a is rotated in the direction to come closer to the lower jaw 11b and closed by the operator holding the handle portion 12 with a hand and squeezing the first handle 12a and the second handle 12b.

A shield portion 24 according to the present modification is a mechanical mechanism that rotates in association with rotation of the upper jaw 11a (for example, rotates integrally with the upper jaw 11a) to switchably open and close the distal end opening 15a. That is, the shield portion 24 opens the distal end opening 15a when the upper jaw 11a is opened with respect to the lower jaw 11b, and closes the distal end opening 15a when the upper jaw 11a is closed.

Turning on and off of the laser light from the optical package 3 in association with opening and closing of the shield portion 24 is as described above.

According to the third embodiment, substantially the same effects as in the first and second embodiments described above can be achieved. In addition, since the shield portion 23 or 24 is provided which can be opened and closed to expose the light emitting face 30a when the dissection device 1 is not performing the dissection operation and to shield the light emitting face 30a when the dissection device 1 is performing the dissection operation, deposition of mist MST on the light emitting face 30a can be prevented by closing the shield portion 23 or 24.

In addition, supply of the laser light from the optical package 3 to the optical fiber 30 is stopped when the dissection device 1 performs the dissection operation, that is, when the shield portion 23 or 24 is closed, application of unnecessary laser light can be avoided, and occurrence of return light of laser light reflected in the dissection device 1 can also be avoided.

[Fourth Embodiment]

Figure 19:
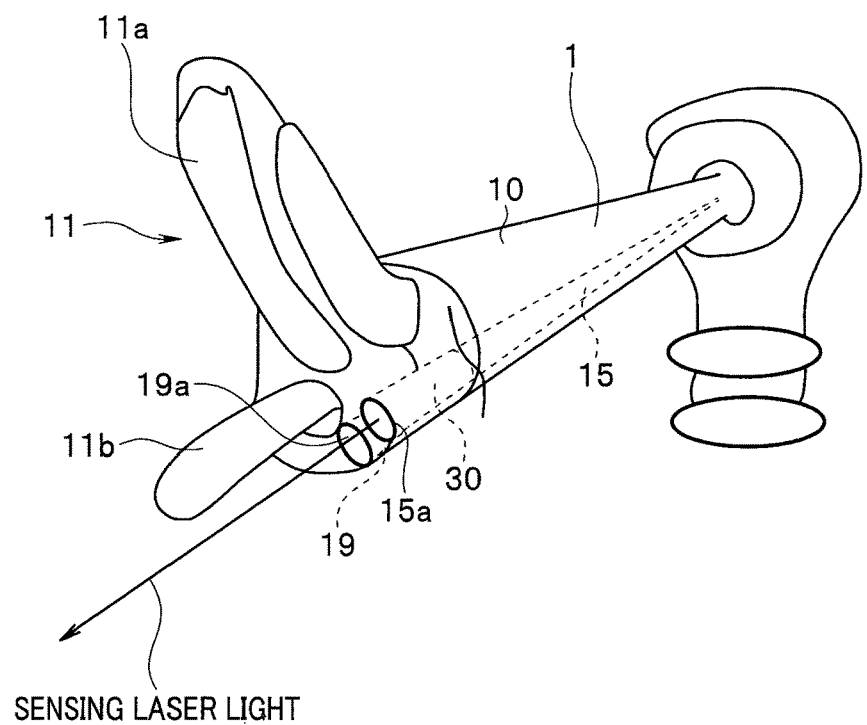
FIG. 19 is a diagram showing the dirt deposition prevention section when the dissection device is not performing the dissection operation in a fourth embodiment of the present invention.
Figure 20:
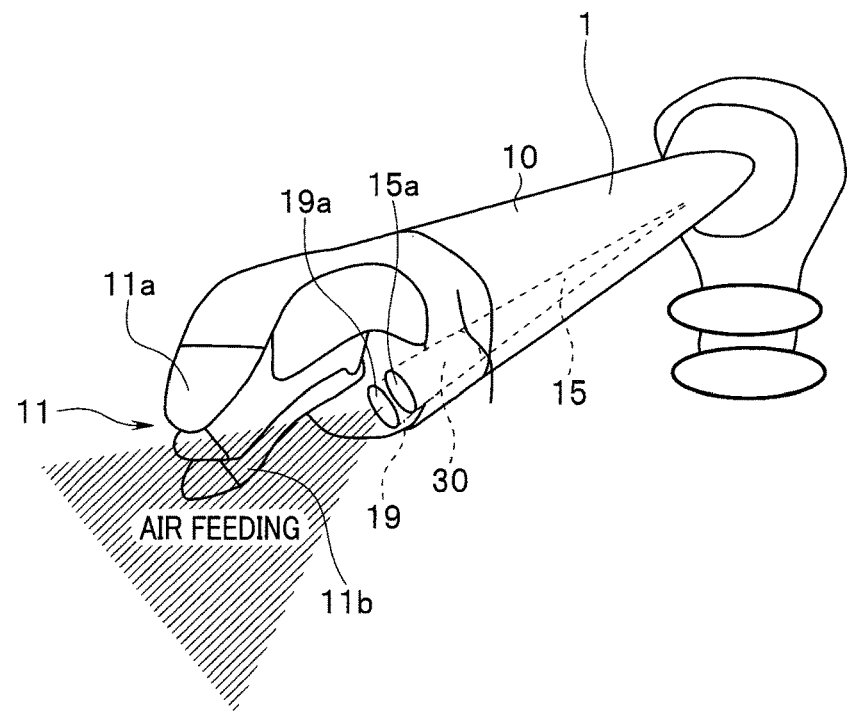
FIG. 20 is a diagram of the dirt deposition prevention section when the dissection device is performing the dissection operation in the fourth embodiment described above.

FIGS. 19 and 20 show a fourth embodiment of the present invention, and FIG. 19 is a diagram showing the dirt deposition prevention section when the dissection device 1 is not performing the dissection operation.

In the description of the fourth embodiment, the same parts as those in the first to third embodiments described above will be denoted by the same reference numerals, and descriptions thereof will be omitted as appropriate, and differences from the first to third embodiments will be mainly described.

In the dissection device 1 according to the present embodiment, not only the optical fiber insertion channel 15 described above but also a fluid channel 19 extending from the hand side to the distal end side is formed. A distal end opening 19a (an opening of the fluid channel 19 in the distal end portion of the dissection device 1) of the fluid channel 19 is preferably disposed close to the distal end opening 15a of the optical fiber insertion channel 15.

The fluid channel 19 can convey a fluid such as a gas or a liquid in both a feeding direction and a suction direction. Thus, for example, when a gas is used as the fluid, the fluid channel 19 doubles as an air feeding channel and an air suction channel (a channel for air suction). When water or other liquid is used as the fluid, the fluid channel 19 doubles as a water feeding channel and a water suction channel.

With such a configuration, when the dissection device 1 performs the dissection operation, air is fed from the fluid channel 19 into a space where the light emitting face 30a emits light to eliminate mist MST in the vicinity of the light emitting face 30a of the optical fiber 30 to prevent the mist MST from being deposited on the light emitting face 30a. Thus, the fluid channel 19 is included in the air feeding/suction unit 52 of the mist reduction unit 5.

FIG. 20 is a diagram of the dirt deposition prevention section when the dissection device 1 is performing the dissection operation.

Air can be fed from the fluid channel 19 to form a so-called air curtain flow in the vicinity of the light emitting face 30a. More specifically, an air curtain flow can be formed between the light emitting face 30a and the upper jaw 11a and lower jaw 11b where cutting or other treatment occurs and mist or the like is produced, thereby preventing the mist or the like from reaching the light emitting face 30a. In this case, the distal end opening 19a of the fluid channel 19 can have a shape suitable for forming the air curtain flow (a slit-like shape, for example).

The air feeding from the fluid channel 19 is performed in association with any of the operations (a), (b) and (c) in the first embodiment described above.

As in the first and third embodiments described above, the blood vessel sensing laser light source 31 and the guide laser light source 32 are automatically turned off in association with the dissection device 1 starting the dissection operation, and laser light is emitted from the optical package 3 in association with the dissection device 1 ending the dissection operation.

Alternatively, as described above with regard to the second embodiment with reference to FIG. 13, the light intensity W of the laser light may be set to fall within the intensity range WR0 where 0≤W<WL in association with the dissection device 1 starting the dissection operation, and set to fall within the intensity range WR1 where WL≤W≤WH in association with the dissection device 1 ending the dissection operation.

Although an example in which the optical fiber insertion channel 15 and the fluid channel 19 are provided as separate channels has been described above, a single channel may be configured to double as the optical fiber insertion channel 15 and the fluid channel 19. In that case, considering that the single channel in which the optical fiber 30 is inserted is used for air feeding (or air suction), the channel can have a diameter greater than the diameter of the optical fiber 30 by a predetermined value (a diameter that allows the channel in which the optical fiber 30 is inserted to feed air). However, as described later with regard to a fifth embodiment, air suction results in introduction of mist into the channel, so that, with the configuration in which a single channel doubles as the optical fiber insertion channel 15 and the fluid channel 19, the optical fiber 30 is preferably removed from inside the channel before air suction is performed.

According to the fourth embodiment, substantially the same effects as in the first to third embodiments described above can be achieved, and dirt can be prevented from being deposited on the light emitting face 30a by feeding air into the space where the light emitting face 30a emits light in association with the dissection operation of the dissection device 1.

In this case, since no mechanical open/close mechanism or the like need to be provided in the vicinity of the treatment portion 11 of the dissection device 1, the dissection device 1 can be reduced in structural complexity and weight, and the manufacturing cost can also be reduced.

In addition, if a single channel doubles as the optical fiber insertion channel 15 and the fluid channel 19, the number of channels is reduced, so that the diameter of the dissection device 1 can be reduced.

[Fifth Embodiment]

Next, a fifth embodiment of the present invention will be described with reference to the drawings described above as required. In the description of the fifth embodiment, descriptions of the same parts as those in the first to fourth embodiments described above will be omitted as appropriate, and differences from the first to fourth embodiments will be mainly described.

According to the present embodiment, the fluid channel 19 in the fourth embodiment described above is used as a suction channel to suck mist MST.

More specifically, when the dissection device 1 performs the dissection operation, the amount of mist MST deposited on the light emitting face 30a is reduced by reducing the concentration of mist MST in the vicinity of the light emitting face 30a by discharging mist MST by sucking air through the fluid channel 19 from the space where the light emitting face 30a emits light.

In this process, mist MST is gathered at the distal end opening 19a of the fluid channel 19 as a result of air suction. Thus, the distal end opening 19a of the fluid channel 19 according to the present embodiment is disposed at the greatest possible distance from the distal end opening 15a of the optical fiber insertion channel 15.

Thus, according to the present invention, no single channel doubles as the optical fiber insertion channel 15 and the fluid channel 19.

In other respects, the fifth embodiment is the same as the fourth embodiment described above. For example, air suction through the fluid channel 19 occurs in association with any of the operations (a), (b) and (c) in the first embodiment described above, and the laser light is turned on and off or the light intensity W is changed in association with the dissection device 1 starting and ending the dissection operation.

According to the fifth embodiment, substantially the same effects as in the first to fourth embodiments described above can be achieved, and dirt deposition on the light emitting face 30a can be alleviated by sucking air from the space where the light emitting face 30a emits light in association with the dissection operation of the dissection device 1.

[Other Embodiments]

Other embodiments of the present invention will be described with reference to the drawings described above as required. In the description of the embodiments, descriptions of the same parts as those in the first to fifth embodiments described above will be omitted as appropriate, and differences from the first to fifth embodiments will be mainly described.

[Other Embodiment E1]

According to another embodiment E1, a heater section such as an electric heater that heats the light emitting face 30a of the optical fiber 30 is provided to heat the light emitting face 30a and its vicinity, thereby preventing solidification of fat.

That is, if fat contained in mist MST is solidified, the fat becomes opaque and causes a serious decrease of the transmittance of the laser light. In view of this, according to the present embodiment, the heater section heats the light emitting face 30a of the optical fiber 30 and its vicinity to keep them at a temperature at which the fat in the mist MST is not solidified (and the optical fiber 30 is not damaged by heat).

As in the embodiments described above, heating by the heater section occurs in association with any of the operations (a), (b) and (c) in the first embodiment described above, and the laser light is turned on and off or the light intensity W is changed in association with the dissection device 1 starting and ending the dissection operation.

The heating by the heater section is preferably combined with the vibration by the vibrator portion 22 described above with regard to the second embodiment, for example. This is because the fat liquefied is effectively removed by vibration. The heating by the heater section can be combined not only with the second embodiment but also with other appropriate embodiments.

According to the other embodiment E1, fat can be more effectively removed.

[Other Embodiment E2]

According to another embodiment E2, grooves having a width of several hundred nanometers to several micrometers (a fractal structure of grooves) are formed in the light emitting face 30a of the optical fiber 30 to increase the repellency to oil in the mist MST.

In this case, a gradient index lens is preferably implemented as a nanostructure (sub-wavelength structure) to provide oil repellency.

The other embodiment E2 can also be combined with other appropriate embodiments.

The other embodiment E2 has an advantage that a mechanical structure, an air feeding/suction unit, and electric power are not required.

[Other Embodiment E3]

According to another embodiment E3, an ITO transparent electrode is mounted on the light emitting face 30a of the optical fiber 30, and a voltage is applied to the ITO transparent electrode to remove oil by electrophoresis.

As in the embodiments described above, the application of the voltage to the ITO transparent electrode occurs in association with any of the operations (a), (b) and (c) in the first embodiment described above, and the laser light is turned on and off or the light intensity W is changed in association with the dissection device 1 starting and ending the dissection operation.

The other embodiment E3 is more effective if the embodiment E3 is combined with the other embodiment E1 (the technique of keeping fat in the liquid state) described above. The other embodiment E3 can be combined with other appropriate embodiments.

The other embodiment E3 has an advantage that a mechanical structure and an air feeding/suction unit are not required, and dirt can be removed by simply applying a voltage.

The portions or sections described above may be configured as a circuit, and any circuit may be implemented as a single circuit or a combination of a plurality of circuits as far as it can serve the same function. Furthermore, any circuit is not limited to a dedicated circuit for serving an intended function and may be a general-purpose circuit that executes a processing program to serve an intended function.

Although a medical apparatus has been mainly described above, the present invention may be a method of operating the medical apparatus in the manner described above, a processing program that makes a computer perform the same processing as the processing performed by the medical apparatus, or a non-transitory computer-readable recording medium that stores the processing program, for example.

The present invention is not limited to the embodiments described above, and various modifications can be made and embodied to the components in implementation of the present invention without departing from the spirit of the present invention. Various aspects of the present invention can be provided by appropriate combinations of a plurality of components disclosed in the above description of embodiments. For example, some of the components shown in an embodiment can be omitted. Furthermore, components from different embodiments can be combined as appropriate. In this way, of course, various modifications and applications are possible without departing from the spirit of the present invention.

What is claimed is:

1. A medical apparatus, comprising:
   a treatment device configured to apply energy to a subject;
   a light emitting surface positioned on the treatment device such that light from the light emitting surface is emitted towards the subject; and
   a shield being movable between a first position configured to expose the light emitting surface to the subject when the treatment device does not perform a treatment operation and a second position to cover the light emitting surface when the treatment device performs the treatment operation.

2. The medical apparatus according to claim 1, further comprising:
   a light source configured to generate laser light and to supply the laser light to the light emitting surface; and
   a controller configured to control the light source to stop the supply of the laser light when the treatment device is performing the treatment operation.

3. The medical apparatus according to claim 1, further comprising:
   a light source configured to generate laser light and supply the laser light to the light emitting surface; and
   a controller configured to control the supply of the laser light to have an output value lower than a service output range when the treatment device does not perform the treatment operation.

4. The medical apparatus according to claim 1, further comprising a vibrator configured to vibrate the light emitting surface.

5. The medical apparatus according to claim 1, wherein the emission of light towards the subject is automatically stopped upon treatment of the subject by the treatment device.

6. The medical apparatus according to claim 5, wherein the shield is connected to the treatment device such that the shield automatically covers the light emission surface upon movement of the treatment device to treat the subject.

* * * * *